_(12)_ United States Patent
Dal Farra et al.

(10) Patent No.: US 7,211,269 B2
(45) Date of Patent: May 1, 2007

(54) COSMETIC OR DERMATOLOGICAL USE OF PEPTIDES FOR PROMOTING ADHESION BETWEEN SKIN CELLS

(75) Inventors: Claude Dal Farra, Opio (FR); Nouha Domloge, Valbonne (FR)

(73) Assignee: Societe d' Extraction de Principes Actifs S.A., Biot (FR)

( * ) Notice: Subject to any disclaimer, the term of this patent is extended or adjusted under 35 U.S.C. 154(b) by 350 days.

(21) Appl. No.: 10/755,277

(22) Filed: Jan. 13, 2004

(65) Prior Publication Data

US 2004/0142873 A1 Jul. 22, 2004

Related U.S. Application Data

(63) Continuation of application No. PCT/FR02/02380, filed on Jul. 8, 2002.

(30) Foreign Application Priority Data

Jul. 13, 2001 (FR) ................... 01 09366

(51) Int. Cl.
*A61K 8/64* (2006.01)
*A61K 38/06* (2006.01)
*A61K 38/08* (2006.01)

(52) U.S. Cl. .................. 424/401; 514/15; 514/17; 514/18

(58) Field of Classification Search ............... None
See application file for complete search history.

(56) References Cited

U.S. PATENT DOCUMENTS 5,380,668 A 1/1995 Herron ............... 436/510
5,849,323 A 12/1998 Braswell et al. ............ 424/439
6,777,389 B1 * 8/2004 Mitts et al. ................... 514/16
2002/0091086 A1 * 7/2002 Vahlne ..................... 514/18

FOREIGN PATENT DOCUMENTS

| DE | 42 44 418 | 7/1993 |
|----|-----------|--------|
| EP | 0 764 444 | 3/1997 |
| FR | 2 784 029 | 4/2000 |
| WO | WO 95/17204 | 6/1995 |

OTHER PUBLICATIONS

Kopple et al., Synthesis and backbone conformations of cyclic hexapeptides cyclo (X-Pro-D-Gin)$^{2n}$, Database accession No. 1983:438803, XP-002198285 abstract, Int. J. Pept. Protein Research, vol. 21, No. 3, 1983.
XP-002198286 & JP 9-157291 abstract, AN 1997-369468, Jun. 17, 1997, Derwent Publications Ltd. London.

* cited by examiner

*Primary Examiner*—Jeffrey Edwin Russel
(74) *Attorney, Agent, or Firm*—Young & Thompson

(57) ABSTRACT

Method for preparing a cosmetic or dermatological composition, of a sufficient amount of peptides of sequence (Gly-Pro-Gln)$_n$-NH$_2$, wherein: n ranges between 1 and 3, and the amino acids can be in the form L, D or DL; the peptides or the composition being designed to: promote adhesion between skin cells, promote cell adhesion, to provide curative and/or preventive treatment for ageing skin symptoms (of physiological or solar origin) and to enhance skin appearance. In a preferred embodiment, the peptide is of sequence (Gly-Pro-Gln)$_2$-NH$_2$.

19 Claims, No Drawings

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE
<221> NAME/KEY: PEPTIDE
<222> LOCATION: (1)..(9)
<223> OTHER INFORMATION: This sequence may encompass 1 to 3 Gly-Pro-Gln
      repeating units

<400> SEQUENCE: 1

Gly Pro Gln Gly Pro Gln Gly Pro Gln
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Pro Gln Gly Pro Gln
 1               5
```

COSMETIC OR DERMATOLOGICAL USE OF PEPTIDES FOR PROMOTING ADHESION BETWEEN SKIN CELLS

The invention concerns the uses for the preparation of a cosmetic or dermatological composition, of a sufficient amount of peptide of sequence (Gly-Pro-Gln)$_n$-NH$_2$ (SEQ ID NO: 1), wherein n ranges between 1 and 3, and where the amino acids can be in the L, D, or DL configuration; the peptides or the composition being designed to:
- promote adhesion between cutaneous cells,
- promote cell adhesion,
- provide curative and/or preventive treatment for aging skin symptoms (of physiological or solar origin) and to enhance skin appearance.

In a preferred embodiment of the invention, said peptide is of the sequence (Gly-Pro-Gln)$_2$-NH$_2$ (SEQ ID NO: 2).

Cutaneous aging is a complex phenomenon due to many intrinsic and extrinsic factors. Clinically, wrinkles and fine lines appear, as well as a loss of cutaneous elasticity, a slackening of cutaneous and subcutaneous tissues . . .

Many ways of research are proposed to fight against aging, such as protection against the environment (sun, pollution . . . ), activation of cellular regeneration, reinforcement of the extracellular matrix (collagen and elastin). Recently, studies have shown the importance of the keratinocytes adhesion on the dermo-epidermal junction in the treatment of skin aging.

In a general way, by increasing cell adhesion between them, and cell-extracellular matrix adhesion, it is possible to prevent, even to treat, the slackening of the skin.

Very few studies have been conducted on this subject despite the fact it offers promising results, whereas the adhesion between the cells and the matrix can support exchanges that we know, now, to be numerous between the cell and its complex environment.

The collagen is a principal element of the extracellular matrix and takes part in skin structure and consistency. Collagen is studies a lot for its many functions and is also abundantly used in cosmetics.

Although the use of collagen was reduced due to BSE problems, collagen still remains very used through marine collagens (native and hydrolysed). Recently, the cosmetic industry was aware of the use of peptides in cutaneous biology (such as sequences derived from alpha-MSH, some neuropeptides), and is in search of peptides having a high activity at the cutaneous level.

Also it is logical to see many studies on peptide sequences trying to imitate the activity of collagen. These sequences try to approach either to a specific area of collagen, or to its very particular form. Need therefore continues to exist for a new derivative of collagen, which has an effect on adhesion on cutaneous cells.

However, the inventors found in a surprising and unexpected way that an effective amount of a peptide of sequence (Gly-Pro-Gln)n-NH$_2$ (SEQ ID NO: 1) has an effect on cell adhesion. It was, heretofore, never described, in the former art, such use of a peptide of sequence (Gly-Pro-Gln)$_n$-NH$_2$ (SEQ ID NO: 1) in cosmetics.

Thus, the main subject of the invention is the use for preparing a cosmetic or dermatological composition, of a sufficient amount of peptide of sequence (Gly-Pro-Gln)$_n$-NH$_2$ (SEQ ID NO: 1), wherein n ranges between 1 an 3, and where the amino acids can be in the L, D, or DL configuration; the peptides or the composition being designed to increase cell adhesion.

More particularly according to the invention, the peptides or the composition are designed to promote adhesion between cutaneous cells.

Thereafter, the term "cellular adhesion" intends, on the one hand, the adhesion between cells and the extracellular matrix, and, on the other hand, the adhesion of cells between them. The term "adhesion between the cutaneous cells", intends, on the one hand, the adhesion between cutaneous cells and the extracellular matrix, and on the other hand, the adhesion of cutaneous cells between them.

The expression "to increase cell adhesion", intends the stimulation of the protein expression aiming at reinforcing cell adhesion and enriching the extracellular matrix with proteins which compose it.

Thus, the peptide or the composition according to the invention, increases the protein expression of the extracellular matrix. There may be mentioned, by way of example of proteins of the extracellular matrix, proteins such as collagen, fibronectin, laminin or elastin. All these proteins are constitutive of the matrix and play a fundamental role.

The laminin-5, for example, interacts with the integrins of basal keratinocytes, which permit thus to anchor the cells on the two-dimensional network of the dermo-epidermal junction.

Cell adhesion is carried out, in particular, thanks to membrane glycoproteins, the integrins. These proteins interact with various molecules of the extracellular matrix, like fibronectin or laminin. They are involved in the keratinocyte adhesion to the extracellular matrix, in the connections between cells and in the basement membrane cohesion of the skin. Thus, an increase in the adherent capacity of the cutaneous cells can indicate an increase of the integrin expression.

Moreover, the reinforcement of the cell adhesion makes it possible to preserve the structure of collagen fibers and to fight cutaneous atrophy due to aging, in particular with photoinduced aging. The peptide, according to the invention, acts on cohesion, communication and on the three-dimensional organization of the cutaneous tissues, thus supporting the fight against the structural disorganization due to cutaneous aging.

Thus, the invention also concerns the uses for preparing a cosmetic or dermatological composition, of an effective amount of peptide of sequence (Gly-Pro-Gln)$_n$-NH$_2$ (SEQ ID NO: 1), wherein n ranges between 1 an 3, and where the amino acids can be in the L, D, or DL configuration; the peptides or the composition being designed to provide curative and/or preventive treatment for aging skin symptoms and to enhance skin appearance.

The expression "to enhance skin appearance" intends all the phenomena which are likely to have for consequences a visual improvement of the skin's aspect. The skin will have a nicer appearance; it will be, for example, much more beautiful, firm and/or smooth. All the small imperfections will be decreased or removed. The papyraceous aspect of the skin, for example, will be attenuated.

The term "cutaneous signs of aging" intends any modification in the external appearance of the skin due to aging, whether chronobiological and/or photoinduced, such as, for example wrinkles and fines lines, withered skin, flabby skin, thinned skin, or lack of elasticity and/or tonicity of the skin, but also all internal modifications of the skin which do not result systematically in a modified external appearance, such as, for example, all internal damages of the skin, particularly to collagen, resulting from ultraviolet radiations exposure.

Skin aging can be, for example, a quantitative and a qualitative deterioration of interactions between the various components of the extracellular matrix, and can result in the appearance of wrinkles and fine lines. These deteriorations are particularly severe in areas exposed to UV. Indeed, fibroblasts exposed to UV adhere slightly more to fibronectin, and has as a consequence a degradation of collagen fibers.

Actually, in a preferred embodiment of the invention, said peptide is of the sequence (Gly-Pro-Gln)$_2$-NH2 (SEQ ID NO: 2).

It may be necessary, for a resistance to degradation, to use a protected form of the peptide according to the invention. Obviously, the form of protection must be a biologically compatible form and must be compatible with use in the cosmetic or the pharmaceutical field.

Many biologically compatible forms of protection can be considered; they are well known by a person skilled in the art, like, for example, the acylation or the acetylation of the N-terminal amine group, or the amidation or the esterification of the terminal carboxyl group.

Thus, the invention relates to the use such as previously defined characterized by the fact that the peptide is in a protected form or not. Preferably, the protection used is either the acylation of the N-terminal amine group, or the esterification of the terminal carboxyl group, or both of them.

In the field of amino acids, the geometry of the molecules is such that they can be theoretically presented as different optical isomers. There is indeed a molecular conformation of the amino acid (AA) such that it deviates on the right the plan of polarization of the light (dextrogyre conformation or D-aa), and a molecular conformation of the amino acid (aa) such that it deviates on the left the plan of polarization of the light (levogyre conformation or L-aa). Nature retained for the natural amino acids only levogyre conformation. Consequently, a peptide of natural origin will be made up only of amino acids of type L-aa.

However, the chemical synthesis in laboratory makes it possible to prepare amino acids having two possible conformations. From this basic material, it is thus possible to incorporate during the peptide synthesis, amino acids in the form of dextrogyre or levogyre optical isomers.

Thus, the amino acids, constituting the peptide according to the invention, can be under configuration L and D; in a preferential way, amino acids have L configuration. Thus, the peptide according to the invention can be in L, D, or DL configuration.

Peptides, the objects of this patent, can be obtained either by traditional chemical synthesis (in solid phase or in homogeneous liquid phase), or by enzymatic synthesis (Kullman and Al, J Biol. Chem. 1980, 225, 8234) from constitutive amino acids or their derivatives. Peptides of this invention can still be obtained by biotechnology (use of a micro-organism, modified or not by genetic engineering); i.e., peptides according to this invention can also be obtained by fermentation of a strain of bacteria, modified or not, by genetic engineering to produce peptides of sequence previously mentioned and their fragments. Peptides of this invention can also be obtained from natural proteins; i.e. by protein extraction of animal or vegetable origin, followed by controlled hydrolysis which releases the peptide fragments of average size and of small size, with the condition that the released elements must contain at least the sequence (Gly-Pro-Gln)-NH$_2$.

It is possible, but non necessary, to carry out the invention to extract either the proteins concerned initially and then to hydrolyse them, or to initially carry out the hydrolysis on raw extract and then to purify the peptide fragments.

Other simpler or more complex processes can be considered by the specialist of the profession who is experienced in synthesis, extraction and purification of proteins and peptides.

Thus, the peptide of the invention may be of natural or synthetic origin. Preferably, the peptide of the invention is obtained by chemical synthesis.

According to another aspect of the present invention, the peptide, mentioned above, is solubilized beforehand in one or more solvents compatible with use in the cosmetic or the pharmaceutical field, such as water, glycol propylene, glycol butylene, diglycols ethoxylated or propoxylated, ethanol, propanol or isopropanol.

According to another aspect of the present invention, the peptide, mentioned above, is solubilized beforehand in one or more vectors such as liposomes or adsorbed on powdery organic polymers, mineral supports like talcs and bentonites, and more generally solubilized in, or fixed on, any vector compatible with use in the cosmetic or the pharmaceutical field.

The composition, according to the invention, can be a cosmetic or a dermatological or a pharmaceutical composition. Preferentially, according to the invention, the composition is a cosmetic composition, because it is intended to improve the aspect and the general cutaneous performances of the skin.

The composition, according to the invention, is preferentially a cosmetic and/or a dermatological composition, adapted to a cutaneous administration, including a medium compatible with a use in the cosmetics or the pharmaceutical field.

Obviously, the invention concerns the mammals in general and, more particularly, human beings.

The effective amount of the active ingredient which can be used according to the invention corresponds to the quantity necessary to obtain the desired result.

To give an order of magnitude, in the cosmetic or dermatological compositions of this invention, the peptide of sequence (Gly-Pro-Gln)n -NH$_2$ (SEQ ID NO: 1) is used in a concentration representing from 0.0005 to 500 ppm (parts per million), and preferentially, in a concentration representing from 0.05 to 50 ppm (parts per million).

To give an order of magnitude, in the cosmetic or dermatological compositions of this invention, the peptide of sequence (Gly-Pro-Gln)$_2$-NH$_2$ (SEQ ID NO: 2) is used in a concentration representing from 0.0005 to 500 ppm (parts per million), and preferentially, in a concentration representing from 0.05 to 50 ppm (parts per million).

Preferentially, the compositions according to the present invention will be in a pharmaceutical form, adapted to a topical use, and cover all the cosmetic or dermatological forms. These compositions must thus contain a medium compatible with use in the cosmetic field, i.e. which is compatible with the skin or hairs.

These compositions can be, in particular, in the form of a cream, a water-in-oil or oil-in-water emulsions, or multiple emulsion, a solution, a suspension, or a powder, adapted to skin, lips and/or hair application.

These compositions can be more or less fluid and have the aspect of a cream, a lotion, a milk, a serum, a pomade, a gel, a paste or a foam. They may also consist of a solid form, such as a stick or they may also be applied on the skin as an aerosol. These compositions can be used as skin-care products and/or as make-up products for the skin.

These compositions can also contain, in a known way, the necessary adjuvants for the formulation, that are common in the corresponding fields, such as solvents, thickeners, thinners, antioxidants, dyestuffs, screening agents, pigments, fillers, preservatives, perfumes or odour absorbers. In any case, these adjuvants and their proportions, will be selected to cause no harm to the properties of the composition. The quantities of these various adjuvants are those conventionally used in the cosmetic field, for example from 0.01 to 20% relative to the total weight of the composition.

When the composition of the invention is an emulsion, the proportion of the fatty phase may range from 5 to 80% by weight, and preferably from 5 to 50% by weight relative to the total weight of the composition. The emulsifiers and coemulsifiers used in the composition are chosen from those conventionally used in the cosmetic field. For example, they may be used in the composition in a proportion ranging from 0.3 to 30% by weight relative to the total weight of the composition.

Of course, the expert will take care to choose the possible complementary compounds, active or inactive ingredients, and/or their quantities, so that the advantageous properties of the mixture are not deteriorated by the addition considered.

Also, an another subject of the invention is a cosmetic or a dermatological composition comprising, in a medium which is compatible with use in the cosmetic or the pharmaceutical field, a sufficient amount of peptide of sequence (Gly-Pro-Gln)$_n$-NH$_2$ (SEQ ID NO: 1). Preferentially, the peptide of said composition has the sequence (Gly-Pro-Gln)$_2$-NH$_2$ (SEQ ID NO: 2).

In the composition according to the invention, the peptide of sequence (Gly-Pro-Gln)$_n$-NH$_2$ (SEQ ID NO: 1) is used in a concentration representing between 0.0005 and 500 ppm (parts per million), and preferably, between 0.05 and 50 ppm (parts per million).

In the composition according to the invention, the peptide of sequence (Gly-Pro-Gln)$_2$-NH$_2$ (SEQ ID NO: 2) is used in a concentration representing between 0.0005 and 500 ppm (parts per million), and preferably, between 0.05 and 50 ppm (parts per million).

The invention, finally, relates to a cosmetic treatment process for the treatment of the manifestations of aging, consisting in skin or hair application of the composition described above.

Other advantages and characteristic of the invention will better appear with the reading of the examples given as an illustrative without limiting it in any way.

EXAMPLE 1

Study of the Stability of the Peptide (Gly-Pro-Gln)$_2$-NH$_2$ (SEQ ID NO: 2)

The Peptide (Gly-Pro-Gln)$_2$-NH$_2$ (SEQ ID NO: 2) was analyzed with a concentration of 10-4 M by HPLC on a column of the C18 type, and with a linear gradient water/TFA 0.1%—acetonitril/TFA 0.1%. After 24 hours at various temperatures (25° C., 37° C. and 60° C.), no decomposition of peptide was observed. Moreover, after 8 days at 25° C., no peptide degradation was obtained.

Human fibroblasts and keratinocytes were cultivated during 24 hours at 37° C. and 5% of $CO_2$. For this period, the cells will release many degradation enzymes in the culture medium. Thereafter, the culture medium is removed to be put in the presence of the peptide. The results of the analyses show that after 24 hours, the peptide presents almost no degradation.

A test is carried out by applying the peptide to the fibroblasts and to the keratinocytes in culture. A HPLC analysis of the culture medium reveals that the peptide concentration decreases quickly, i.e. in a few hours.

These results, taken as a whole, suggest the possibility of a penetration of peptide in the cell. This assumption is then consolidated by the tests of effectiveness exposed in the

EXAMPLE 2

Effects of the Peptide of the Example 1 on Adhesion Between the Cutaneous Cells

The study is carried out in 96 wells micro-plates on keratinocytes cultured in an incubator at 37° C. and 5% of $CO_2$. The wells of these plates are pre-treated, for 12 hours, in different ways; four conditions have been realized:

Condition A: negative control, not containing peptide;
Condition B: incubated with various peptides, made up from 3 to 25 amino acids, with a concentration of 35 ppm;
Condition C: incubated with collagen of the type I with a concentration of 60 ppm;
Condition D: incubated with the peptide of sequence (Gly-Pro-Gln)$_2$-NH$_2$ (SEQ ID NO: 2) to a concentration of 5 ppm.

After 3 hours of contact with the keratinocytes, the wells are completely filled with medium, hermetically closed, turned over and agitated on a three-dimensional agitator during 20 minutes. Then the plates are emptied and the remaining medium is aspired. Then, 100 µl of MTT with 1 mg/ml are added by wells and are left for 3 hours at 37° C. and 5% $CO_2$. The solution is finally withdrawn, then 100 µl of DMSO is added. A reading of the OD is made at 560 nm against 630 nm.

The results show various Optical Densities (OD) obtained according to the various conditions. The OD is proportional to the quantity of viable cells, i.e. which adhered to the micro-plates.

|  | Conditions | | | |
| --- | --- | --- | --- | --- |
|  | A | B | C | D |
| O.D. | 0.490 | 0.490 | 0.680 | 0.620 |

These results show, that only after 3 hours of contact with the keratinocytes, the peptide of sequence (Gly-Pro-Gln)$_2$-NH$_2$ (SEQ ID NO: 2) brings a good cell adhesion, similar to that of the collagen of the type I, although the peptide was used in a lower concentration than collagen (10 times lower).

EXAMPLE 3

Examples of Composition According to the Invention

These compositions were obtained by simple mixture of the various components. The quantities indicated are percentages by weight.

1—Oil-in-Water Emulsion

Oily phase:

| | |
| --- | --- |
| Cetearyl Alcohol (and) Cetearyl Glucoside | 5.00% |
| Jojoba Oil | 5.00% |
| Mineral Oil | 5.00% |
| Isopropyl Palmitate | 7.00% |

Aqueous phase:

| | |
| --- | --- |
| Glycerin | 5.00% |
| Allantoin | 0.10% |
| Peptide of example 1 | 1 ppm |
| Polyacrylamide (and) C13–14 Isoparaffin (and) Laureth-7 | 0.30% |
| Preservative | 0.50% |
| Fragrance | 0.50% |
| Water | qs 100% |

2—Gel

| | |
| --- | --- |
| Carbomer (solution 2%) | 25.00% |
| Triethanolamine | 0.50% |

-continued

| | |
|---|---|
| Peptide of example 1 | 0.1 ppm |
| Preservative | 0.20% |
| EDTA | 0.10% |
| Fragrance | 0.50% |
| Water | qs 100% |

3—Lotion

| | |
|---|---|
| Propylen Glycol | 1.00% |
| Allantoin | 0.30% |
| Glycerin | 1.00% |
| PEG-7 Glyceryl Cocoate | 1.00% |
| Peptide of example 1 | 10 ppm |
| Preservative | 0.20% |
| Fragrance | 0.50% |
| Water | qs 100% | n-$NH_2$ (SEQ ID NO: 1), wherein n ranges between 1 an 3, and the amino acids can be in the L, D, or DL configuration.

3. The method as defined in claim 1, wherein said peptide is of the sequence (Gly-Pro-Gln)$_2$-$NH_2$ (SEQ ID NO: 2).

4. The method as defined in claim 1, wherein said peptide is used in a composition at a concentration between 0.0005 and 500 ppm of the said peptide.

5. The method as defined in claim 1, wherein said peptide is used in a composition at a concentration between 0.05 and 50 ppm of the said peptide.

6. The method as defined in claim 1, wherein said peptide is solubilized beforehand in one or more solvents compatible with use in the cosmetic or the pharmaceutical field.

7. The method as defined in claim 1, wherein said peptide is solubilized beforehand in one or more vectors compatible with use in the cosmetic or the pharmaceutical field.

8. The method as defined in claim 2, wherein said peptide is used in a composition at a concentration between 0.0005 and 500 ppm of the said peptide.

The invention claimed is:

1. A method for treating cutaneous signs of aging and for enhancing skin appearance, comprising administrating a composition comprising an effective amount of peptide of sequence (Gly-Pro-Gln)n-$NH_2$ (SEQ ID NO: 1), wherein n ranges between 1 an 3, and the amino acids can be in the L, D, or DL configuration.

2. A method for improving cell adhesion between skin cells, comprising applying to skin a composition comprising an effective amount of a peptide of sequence (Gly-Pro-Gln)

9. The method as defined in claim 2, wherein said peptide is used in a composition at a concentration between 0.05 and 50 ppm of the said peptide.

10. The method as defined in claim 6, wherein said solvent or solvents are selected from the group consisting of water, propylene glycol, butylene glycol, ethoxylated or propoxylated diglycols, ethanol, propanol, and isopropanol.

11. The method as defined in claim 1, wherein said peptide is fixed on a vector or vectors.

12. The method as defined in claim 7, wherein said peptide is solubilized in liposomes.

13. The method as defined in claim 11, wherein said peptide is adsorbed on powdery organic polymers or mineral supports.

14. The method as defined in claim 13, wherein said mineral supports are talcs or bentonites.

15. A method for treating cutaneous signs of aging and for enhancing skin appearance, comprising administrating a composition comprising an effective amount of peptide of SEQ ID NO: 1, wherein said peptide is in a protected form or not, and the amino acids of the peptide can be in the L, D, or DL configuration.

16. The method as defined in claim 15, wherein said peptide is in a protected form.

17. The method as defined in claim 16, wherein the peptide sequence further comprises a terminal carboxyl group that forms an ester or an amide.

18. The method as defined in claim 16, wherein the peptide further comprises a terminal amine group that is acylated or acetylated.

19. The method as defined in claim 15, wherein said peptide comprises SEQ ID NO: 2.

* * * * *